United States Patent
Kim et al.

(10) Patent No.: US 9,410,127 B2
(45) Date of Patent: Aug. 9, 2016

(54) MICROFLUIDIC APPARATUS AND METHOD OF ENRICHING TARGET MATERIAL IN BIOLOGICAL SAMPLE BY USING THE SAME

(71) Applicant: Samsung Electronics Co., Ltd., Suwon-si, Gyeonggi-do (KR)

(72) Inventors: Min Seok S Kim, Yongin-si (KR); Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 119 days.

(21) Appl. No.: 13/941,117

(22) Filed: Jul. 12, 2013

(65) Prior Publication Data
US 2014/0154664 A1    Jun. 5, 2014

(30) Foreign Application Priority Data
Dec. 4, 2012    (KR) .................. 10-2012-0139833

(51) Int. Cl.
*C12N 5/09*    (2010.01)
*C12N 15/10*    (2006.01)
*B01L 3/00*    (2006.01)

(52) U.S. Cl.
CPC .......... *C12N 5/0693* (2013.01); *B01L 3/502753* (2013.01); *C12N 15/1006* (2013.01); *B01L 2200/0621* (2013.01); *B01L 2200/16* (2013.01); *B01L 2300/0803* (2013.01);
(Continued)

(58) Field of Classification Search
CPC ............ B01L 3/5027; B01L 3/502746; B01L 3/502753; B01L 2300/0621; B01L 2300/0803; B01L 2400/0409

USPC .................. 422/502, 503, 506, 507
See application file for complete search history.

(56) References Cited

U.S. PATENT DOCUMENTS 6,632,399 B1 * 10/2003 Kellogg .............. B01F 13/0059
                                                              422/505
7,857,141 B2    12/2010 Park et al.
(Continued)

FOREIGN PATENT DOCUMENTS

EP    0965388 A2    12/1999
EP    2737948 A1    6/2014
(Continued)

OTHER PUBLICATIONS

EPO Extended Search Report in Application No. 13178795.4 dated Jul. 21, 2014.
(Continued)

*Primary Examiner* — Jill Warden
*Assistant Examiner* — Dwayne K Handy
(74) *Attorney, Agent, or Firm* — Leydig, Voit & Mayer, Ltd.

(57) ABSTRACT

A micro fluidic apparatus includes a sample chamber that divides a sample into a first fluid layer and a second fluid layer due to a centrifugal force; a first enriching unit a that receives the first fluid layer from the sample chamber, forms a first complex of a first fine particle and the first target material, and separates the first complex from the first fluid layer using a density difference; and a second enriching unit that receives the second fluid layer from the sample chamber, forms a second complex of a second fine particle and the second target material, and separates the second complex from the second fluid layer using a density difference.

14 Claims, 8 Drawing Sheets

(52) U.S. Cl.
CPC . *B01L 2300/0864* (2013.01); *B01L 2400/0409* (2013.01); *B01L 2400/0677* (2013.01); *B01L 2400/086* (2013.01)

(56) References Cited

U.S. PATENT DOCUMENTS

| | | |
|---|---|---|
| 2004/0018116 A1* | 1/2004 | Desmond et al. .............. 422/58 |
| 2005/0130177 A1 | 6/2005 | Bedingham et al. |
| 2010/0151560 A1 | 6/2010 | Wo et al. |
| 2011/0020194 A1 | 1/2011 | Lee et al. |
| 2011/0129856 A1 | 6/2011 | Park et al. |
| 2011/0217729 A1 | 9/2011 | Hong |

FOREIGN PATENT DOCUMENTS

| | | |
|---|---|---|
| KR | 1020090020086 A | 2/2009 |
| KR | 1020110088746 A | 8/2011 |

OTHER PUBLICATIONS

Ducree et al., "The centrifugal microfluidic Bio-Disk platform", *Journal of Micromechanics and Microengineering*, 17: S103-S115 (2007).

Lee et al, "Fully integrated lab-on-a-disc for simultaneous analysis of biochemistry and immunoassay from whole blood", *Lab Chip* 11:70-78 (2011).

* cited by examiner

MICROFLUIDIC APPARATUS AND METHOD OF ENRICHING TARGET MATERIAL IN BIOLOGICAL SAMPLE BY USING THE SAME

CROSS-REFERENCE TO RELATED APPLICATIONS

This application claims the benefit of Korean Patent Application No. 10-2012-0139833, filed on Dec. 4, 2012, in the Korean Intellectual Property Office, the entire disclosure of which is incorporated herein by reference.

BACKGROUND

1. Field

The present disclosure relates to microfluidic apparatuses for isolating target cells in a biological sample and methods of enriching a target material by using the microfluidic apparatus.

2. Description of the Related Art

Death of a patient caused by a malignant tumor is typically due to metastasis of the tumor from a site where the tumor originally occurred to other tissues or organs. Accordingly, in order to increase the chances of survival, it is very important to discover tumor metastasis early. In general, cancer is diagnosed by histopathology. Histopathology is a diagnosis method wherein a tissue sample obtained from a biopsy specimen is used to directly identify tumor cells. However, a biopsy specimen only provides information about the tissue contained in the biopsy specimen, such that a biopsy specimen may not generally be used to identify tumor metastasis. Accordingly, the use of histopathology in diagnosing or monitoring tumors, especially metastasized tumors, has many limitations.

Circulating tumor cells (CTCs) can be identified in patients before a tumor is originally detected, and CTCs may play an important factor in early diagnosing cancer. In addition, since cancer may spreads through blood, CTCs may be a marker for identifying cancer metastasis. In addition, when CTCs can be detected after a tumor is removed by a surgical operation, the possibility of recurrence of cancer is very high. However, since the amount of CTCs in blood may be very small and since CTCs are very fragile, it is difficult to correctly quantify CTCs. Accordingly, there is a need to develop a diagnosis method with high sensitivity in detecting CTCs, cancer cells, or cancer stem cells present in the body of patients.

SUMMARY

Provided are microfluidic apparatuses for separating and enriching two different target materials in a biological sample according to an automated process, and methods of enriching the target materials by using the microfluidic apparatus.

Additional aspects will be set forth in part in the description which follows and, in part, will be apparent from the description, or may be learned by practice of the presented embodiments.

According to an aspect, a microfluidic apparatus is mounted on a rotation driving unit and induces a fluid to flow due to a centrifugal force. The microfluidic apparatus includes a sample chamber housing a biological sample, the biological sample being separated into a first fluid layer including a first target material and a second fluid layer including a second target material due to a centrifugal force in the sample chamber; a first enriching unit that receives the first fluid layer from the sample chamber, forms a first complex, in which a first fine particle and the first target material are connected, and separates the first complex from the first fluid layer using a density difference with a density-gradient material (DGM) with a lower density than the first complex; and a second enriching unit that receives the second fluid layer from the sample chamber, forms a second complex, in which a second fine particle and the second target material are connected, and separates the second complex from the second fluid layer using a density difference between the second fluid layer and the second complex.

The first enriching unit may include a first particle chamber that houses the first fine particle and is connected to the sample chamber by a first sample channel to form the first complex in the first particle chamber; a separation chamber that houses the DGM and is connected to the first particle chamber by a separation channel to locate the first complex in the lowest layer of the separation chamber from a rotation center of the microfluidic apparatus using a density difference; and a first recovering chamber that is connected to the separation chamber by a first recovering channel to recover the first complex through the first recovering channel.

The first enriching unit may further include a first waste chamber that is connected to the separation chamber by a first discharge channel to discharge an upper layer material of the first complex through the first discharge channel.

The first enriching unit may further include a first cleaning solution chamber that houses a first cleaning solution and is connected to the separation chamber by a first cleaning channel; and a first waste chamber that is connected to the separation chamber by a plurality of connection channels, which sequentially open and close, to discharge the upper layer material of the first complex and the first cleaning solution.

The second enriching unit may further include a second particle chamber that houses the second fine particle and is connected to the sample chamber by a second sample channel to form and locate the second complex in the lowest layer of the microfluidic apparatus from a rotation center; and a second recovering chamber that is connected to the second particle chamber by a second recovering channel to recover the second complex through the second recovering channel.

The second enriching unit may further include a second waste chamber that is connected to the second chamber by a second discharge channel to discharge an upper layer material of the second complex through the second discharge channel.

The second enriching unit may further include a second cleaning solution chamber that houses a second cleaning solution and is connected to the second particle chamber by a second cleaning channel; and the second waste chamber that is connected to the second particle chamber by a plurality of connection channels, which sequentially open and close, to discharge the upper layer material of the second complex and the second cleaning solution.

The sample may be blood, such that the first fluid layer may be a white blood cell layer, and the second fluid layer may be a plasma layer. The first target material may be a circulating tumor cell, a cancer stem cell, or a cancer cell. The second target material may be nano (or micro)-vesicles, miRNA, DNA, or sub-micron sized lipid particles.

A partition wall may be provided in the sample chamber to form a bottleneck portion together with at least one of a top wall and a bottom wall of the sample chamber to partially restrict the flow of the biological sample in a radial direction of the sample chamber, and a gap between the bottleneck portion and the at least one of the top wall and the bottom wall may be greater than a gap inducing a capillary phenomenon.

A plurality of the partition walls may be arranged in a circumference direction of the sample chamber and the partition walls may be spaced apart from each other with an opening therebetween.

Each of the openings may be narrower from an inner portion of the sample chamber to an outer portion of the sample chamber in the radial direction.

According to another aspect, a method of enriching a target material by using a microfluidic apparatus that induces a flow of a fluid housed therein due to a centrifugal force includes forming a first fluid layer that includes a first target material and a second fluid layer that includes a second target material by centrifuging the sample in a sample chamber of the microfluidic apparatus; transporting the first and second fluid layers to first and second enriching units, respectively; mixing a first fine particle that is specifically connected to a surface marker of the first target material with the first fluid layer to form a first complex in which the first target material and the first fine particle are connected, and separating the first complex from the first fluid layer by using a DGM with a density that is less than the density of the first complex but greater than the density of the first fluid layer; mixing a second fine particle that is specifically connected to a surface marker of the second target material with the second fluid layer to form a second complex in which the second target material and the second fine particle are connected, and separating the second complex from the second fluid layer using a density difference between the second complex and the second fluid layer; and transporting the first and second complexes to first and second recovering chambers, respectively.

The method may further include discharging an upper layer material of the first complex and an upper layer material of the second complex to first and second waste chambers, respectively, before the transporting of the first and second complexes to the first and second recovering chambers.

The method may further include cleaning the first and second complexes by supplying first and second cleaning solutions to the first and second enriching units, respectively after the discharging of the upper layer material of the first complex and the upper layer material of the second complex to the first and second waste chambers, respectively, and discharging the first and second cleaning solutions to the first and second waste chambers.

The sample may be blood, the first fluid layer may be a white blood cell layer, and the second fluid layer may be a plasma layer. The first target material may be a circulating tumor cell, a cancer stem cell, or a cancer cell. The second target material may be nano (or micro)-vesicles, miRNA, DNA, or sub-micron sized lipid particles.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
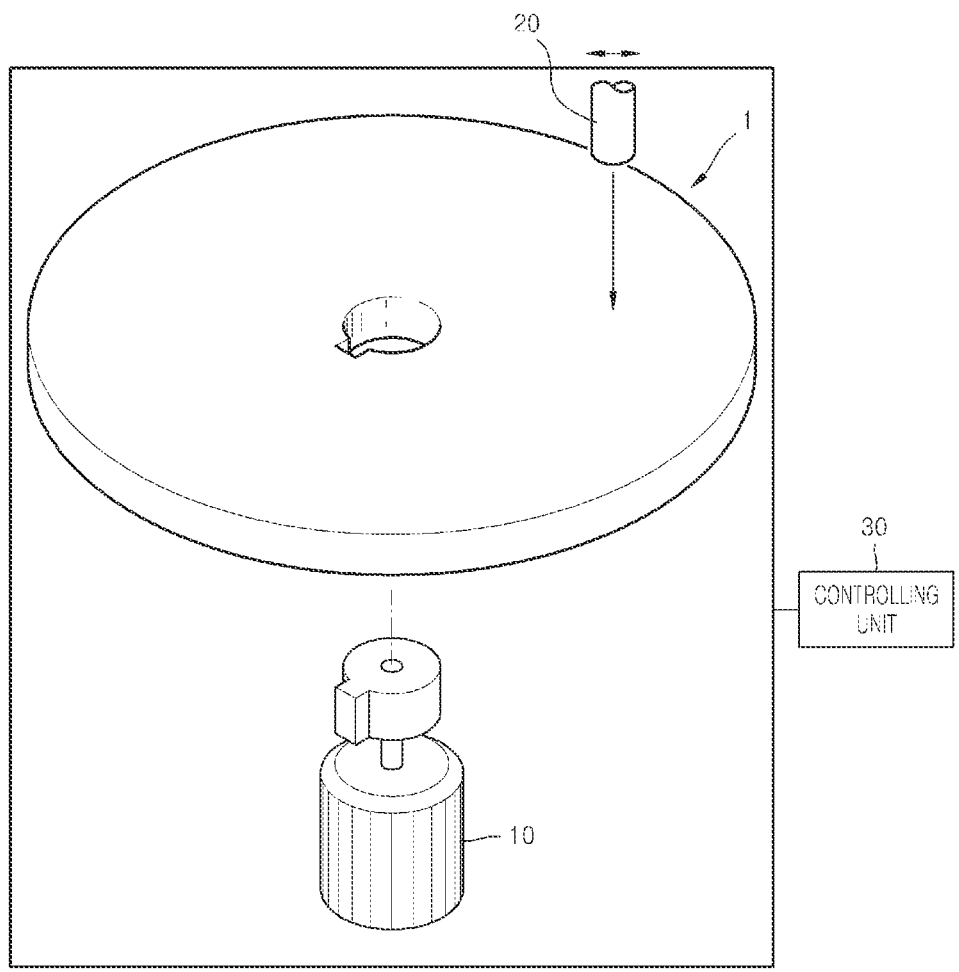
FIG. 1 is a schematic diagram of a cell enrichment system according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Hereinafter, embodiments are described in detail with reference to the attached drawings. These embodiments are presented herein for illustrative purpose only, and the scope is not limited thereto.

FIG. 1 illustrates an example of a target material enrichment system including a microfluidic apparatus 1 according to an embodiment. FIG. 1 illustrates a rotation driving unit 10 and an electromagnetic wave generator 20. The rotation driving unit 10 rotates the microfluidic apparatus 1 to provide a centrifugal force for centrifuging a sample and moving a fluid. The rotation driving unit 10 may stop the microfluidic apparatus 1 from rotating at a predetermined location such that the valves in the microfluidic apparatus 1 face the electromagnetic wave generator 20. The electromagnetic wave generator 20 is used to operate the valves of the microfluidic apparatus 1. The electromagnetic wave generator 20 may, for example, irradiate a laser beam. The electromagnetic wave generator 20 may move in a radial direction of the microfluidic apparatus 1. Although not illustrated in FIG. 1, the rotation driving unit 10 may include a motor drive apparatus that controls an angular position of the microfluidic apparatus 1 to align the valves of the microfluidic apparatus 1 and the electromagnetic wave generator 20. For example, the motor drive apparatus may be a step motor or a direct current motor. A reference numeral 30 denotes a controlling unit for controlling an enriching process.

Figure 2:
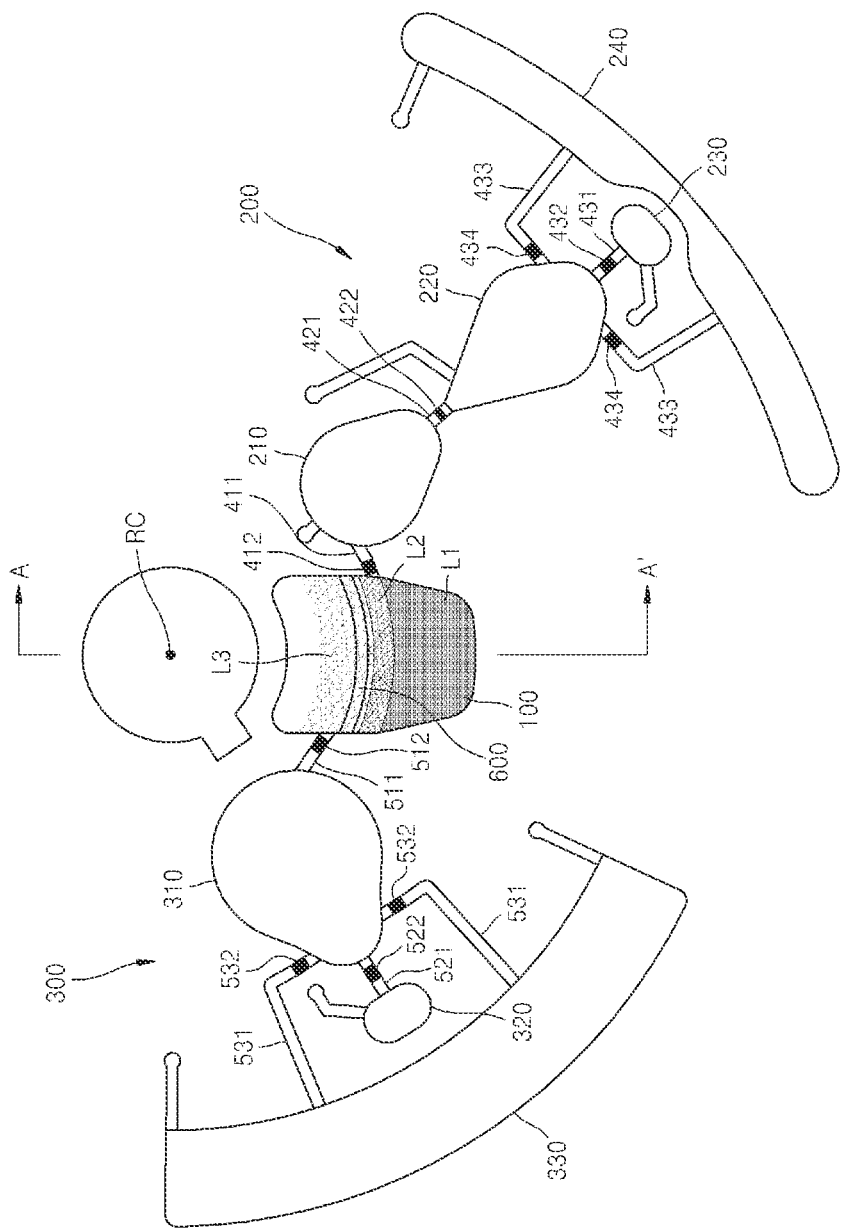
FIG. 2 is a perspective view of a microfluidic apparatus according to an embodiment from which a top plate is removed.

FIG. 2 is a perspective view of the microfluidic apparatus 1 not including a top plate. The microfluidic apparatus 1 according to the present embodiment induces flow of a fluid housed therein due to a centrifugal force. The microfluidic apparatus 1 includes a microfluidic structure for providing a space for housing a fluid and a passage of the fluid. The microfluidic apparatus 1 may have, for example, a rotatable disc shape, but is not limited thereto.

The microfluidic apparatus 1 may be formed of a plastic material, such as acryl, that is moldable and has a biologically inactive surface, or an organic silicon material, such as PEWS. However, a material for the microfluidic apparatus 1 is not limited thereto, and may be any one of various materials that have chemical and biological stabilities, optical transparency, and mechanical processability. The microfluidic apparatus 1 may include a plurality of plates. A concaved structure corresponding to a chamber or a channel is formed at a contact surface of the plates, and the plates are combined with each other to form a space for housing a fluid and a passage for the fluid inside the microfluidic apparatus 1. For example, the microfluidic apparatus 1 may have a double-plate structure including a top plate and a bottom plate according to an embodiment. However, according to another embodiment, the microfluidic apparatus 1 may have a triple-plate structure including a top plate, a bottom plate, and a partition plate defining a microfluidic structure. The plates may be combined by using an adhesive or a double-side adhesive tape, or by ultrasonic wave fusing or laser fusing.

The microfluidic apparatus 1 may have a single microfluidic structure or a plurality of microfluidic structures. For example, the microfluidic apparatus 1 may be divided into a few regions, each of which may include a microfluidic structure that operates independently. A microfluidic structure prepared on one region is illustrated in FIG. 2.

The microfluidic apparatus 1 according to an embodiment may enrich different target materials included in a biological sample. Referring to FIG. 2, a first enriching unit 200 for enriching a first target material from the biological sample and a second enriching unit 300 for enriching a second target material from the sample are illustrated. A sample chamber 100 is extended in a radial direction from a rotation center RC. The sample chamber 100 may have an inlet (not shown) for loading the sample into the sample chamber 100. The sample is centrifuged in the sample chamber 100 as the microfluidic apparatus 1 rotates.

The first target material may be a target cell in blood. For example, the target cell may be circulating tumor cell (CTC), a cancer stem cell, or a cancer cell. The target cell may be, for example, a cancer or tumor cell selected from the group consisting of bladder cancer, breast cancer, uterine cervical cancer, cholangiocarcinoma, colorectal cancer, uterine endometrial cancer, esophageal cancer, stomach cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, glioblastoma/astrocytoma, melanoma, mesothelioma, and Wilms' tumor.

The second target material may be a protein in blood, such as nano (or micro)-vesicles, micro RNA (miRNA), DNA, or sub-micron sized lipid particles.

The biological sample may be any biological sample that includes the first and second target materials. For example, the biological sample may be selected from the group consisting of a biopsy sample, a tissue sample, a cell suspension in which a separated cell is suspended in a liquid medium, a cell culture, and a combination thereof. The biological sample may be selected from the group consisting of blood, bone marrow, saliva, lachrymal fluid, urine, semen, mucous fluid, and a combination thereof. For example, blood may be used as a sample to separate CTCs and miRNA. For example, when blood is centrifuged, a lowest layer is a red blood cell layer L1, and then a white blood cell layer (buffy coat) (a first fluid layer) L2, and a plasma layer (a second fluid layer) L3 are sequentially layered on the red blood cell layer L1. The target cell may be mostly located in the white blood cell layer L2, and proteins in the blood are mostly located in the plasma layer L3. In this regard, the first and second enriching unit 200 and 300 may be connected to the sample chamber 100 at different locations from the rotation center RC in a radial direction, and thus the first and second enriching unit 200 and 300 may be respectively provided with the white blood cell layer L2 and the plasma layer L3 to respectively separate and enrich the target cell and protein in the blood.

[The First Enriching Unit]

Referring to FIG. 2, the first enriching unit 200 receives the first fluid layer including the first target material from the sample chamber 100, and separates the first target material from the first fluid layer. In the first enriching unit 200, first fine particles are attached to the first target material and form a first target material-first fine particle complex, i.e., a first complex, and a density gradient medium (DGM) is used to separate the first complex from the first fluid by using a density difference. In this regard, the first enriching unit 200 includes a first particle chamber 210 housing the first fine particles and a separation chamber 220 housing the DGM.

At least one ligand that is specific to a surface marker of the first target material may be connected to a first fine particle. The first fine particle may bind to the first target material to increase the density of the first target material. The first fine particle may have a density that may cause a difference between the density of the first target material in the sample and the density of the remaining materials other than the first target material. For example, when blood containing a cancer cell as the first target material is used as a biological sample, since densities of a white blood cell and a red blood cell are respectively about 1.05 g/cm$^3$ and about 1.1 g/cm$^3$, the first fine particle with an appropriate density may be selected in consideration of such densities. The first fine particle may be, for example, selected from the group consisting of a polystyrene particle, a polymethylmetaacrylate particle, a latex particle, an acrylonitril-butadiene-styrene copolymer (ABS) particle, a cyclic olefin copolymer particle, a melamine particle, and a composite thereof, but is not limited thereto. A diameter of the fine particle may vary according to a target cell to be separated and a fine particle to be used, and may be, for example, in a range of about 1 nm to about 100 µm, or about 10 nm to about 10 µm. The first fine particle may be a microparticle or a nanoparticle. The first fine particle may be a magnetic particle or a non-magnetic particle.

The surface marker may be selected from the group consisting of protein, sugar, lipid, nucleic acid, and a combination thereof. For example, the surface marker may be a protein, i.e., an antigen, which is specifically expressed in cancer or tumor cell and is displayed on a cell membrane, and for example, may be EpCAM, c-Met, cytokeratines, CD45, Her2, or a combination thereof. In addition, the ligand that is specific to the surface marker may be an antibody that specifically binds an antigen protein.

The DGM is used to separate the first complex from the first fluid including the first complex based on a density gradient. DGM is a material with a density that is less than the density of the first complex but greater than the density of the first fluid layer. DGM may be, for example, Ficoll, Percoll, polysaccharide, NaCl solution, or the like.

The first particle chamber 210 is connected to the sample chamber 100 via a first sample channel 411. A first sample valve 412 is prepared in the first sample channel 411 to control the flow of a fluid. The first sample valve 412 may be a normally closed valve that opens the first sample channel 411 when energy is supplied from the outside while the first sample channel 411 is closed. The first target material and the first fine particle contact each other in the first particle chamber 210, and as first fine particles are attached to the first target material, the first target material-first fine particle complex (the first complex) is formed. The first particle chamber 210 may have an inlet (not shown) for loading the first fine particles. When the microfluidic apparatus 1 is manufactured for a predetermined task, first fine particles suitable for the task may be housed in advance in the first particle chamber 210 in the manufacturing procedure of the microfluidic apparatus 1.

The separate chamber 220 is connected to the first particle chamber 210 via a separation channel 421. A separation valve 422 is prepared in the separation channel 421 to control the flow of a fluid. The separation valve 422 may be a normally closed valve. The DGM is housed in the separation chamber 220. An inlet (not shown) for loading the DGM may be prepared in the separation chamber 220. When the microfluidic apparatus 1 is manufactured for a predetermined task, DGM suitable for the task may be housed in advance in the separation chamber 220 in the manufacturing procedure of the microfluidic apparatus 1. The separation chamber 220 is disposed at the outside of the first particle chamber 210 in a radial direction from the rotation center RC so as fluid may flow from the first particle chamber 210 to the separation chamber 220 due to a centrifugal force. The first complex and the first fluid layer are separated with the DGM therebetween in the separation chamber 220. The first complex gathers at the lowest layer of the separation chamber 220, i.e., the outermost side in a radial direction from the rotation center RC. An extraction hole (not shown) may be provided in the separation chamber 220 to extract the first complex. For example, the first complex gathered at the lowest layer of the separation chamber 220 may be extracted through an extraction hole by using, for example, a pipette, and thus the first complex may be separated from the fluid. In this regard, the first target material existing in a very small amount in the sample may be separated and enriched.

A first enriching unit 200 may further include a first recovering chamber 230 housing the first complex. The first recovering chamber 230 is connected to the separation chamber 220 via a first recovering channel 431. A recovering valve 432 is provided in the first recovering channel 431 to control the flow of a fluid. The first recovering valve 432 may be a normally closed valve. Also, the first recovering valve 432 may be an open-close valve that opens the first recovering channel 431 when energy is supplied from the outside, and closes the first recovering channel 431 when energy is supplied again. The first recovering chamber 230 is disposed outside the separation chamber 220 in the radial direction from the rotation center RC. In the separation chamber 220, the first complex gathers in the lowest layer, and when the first recovering channel 431 is opened by using the first recovering valve 432, the first complex flows into the first recovering chamber 230 due to a centrifugal force. For example, the first complex gathered in the first recovering chamber 230 may be extracted through the extraction hole by using, for example, a pipette, and thus the first complex may be separated from the fluid. When the first recovering valve 432 is an open-close valve, the first recovering channel 431 may be closed before recovering the first complex from the first recovering chamber 230.

The first enriching unit 200 may further include a first waste chamber 240. The first waste chamber 240 may be connected to the separation chamber 220 by a first discharge channel 433. A first discharge valve 434 may be provided in the discharge channel 433 to control the flow of a fluid. The first discharge valve 434 may be a normally closed valve. The first discharge channel 433 is provided to discharge a material including DGM, in upper layers that are located on a top of the lowest layer including the first complex, among the layers separate by the centrifugation in the separation chamber 220. Therefore, the first discharge channel 433 is connected to the separation chamber 220 that is located closer to the rotation center RC than the first recovering channel 431. Due to such a structure, the material in upper layers other than the first complex gathered in the lowest layer of the separation chamber 220 may be discharged to the first waste chamber 240 through the first discharge channel 433, and then, the first complex may be recovered to the recovering chamber 230 by opening the first recovering channel 431.

Figure 3:
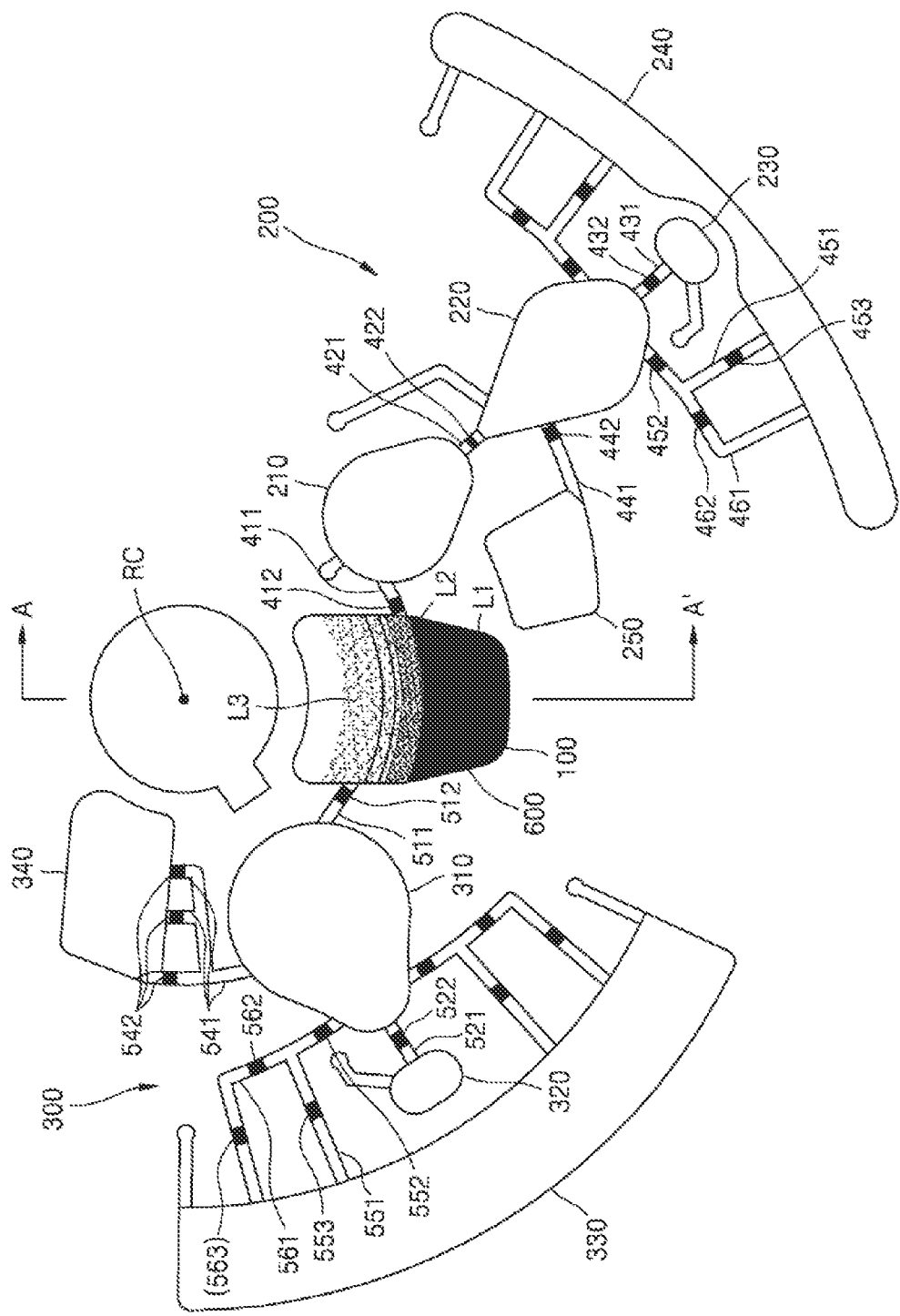
FIG. 3 is a perspective view of a microfluidic apparatus according to another embodiment from which a top plate is removed.

Referring to FIG. 3, the first enriching unit 200 may further include a first cleaning solution chamber 250. A first cleaning solution is housed in the first cleaning solution chamber 250. The first cleaning solution is provided to increase a degree of purity of the first complex before recovering the first complex to the first recovering chamber 230. The first cleaning solution chamber 250 is connected to the separation chamber 220 by a first cleaning channel 441. A first cleaning valve 442 is prepared in the cleaning channel 441 to control the flow of a fluid. The first cleaning valve 442 may be a normally closed valve. In this regard, the first discharge channel 433 may include a first connection channel 451 connecting the separation chamber 220 and the first waste chamber 240, and a second connection channel 461 that is branched from the first connection channel 451 and connected to the first waste chamber 240. Valves 452 and 453 may be prepared at different locations in the first connection channel 451. The valve 452 located closer to the separation chamber 220 may be a normally closed valve, the valve 453 relatively far from the separation chamber 220 may be a normally open valve that closes the first connection channel 451 when energy is supplied from the outside while the first connection channel 451 is opened. The second connection channel 461 is branched from the first connection channel 451 between the valves 452 and 453. A valve 462 is prepared in the second connection channel 461. The valve 462 is a normally closed valve.

Due to such a structure, when the first complex gathers in the lowest layer of the separation chamber 220 based on a density gradient, the first connection channel 451 may be opened by using the valve 452, and thus a material in the upper layers on the lowest layer, such as the DGM, may be discharged to the first waste chamber 240 through the first connection channel 451. Then, the first connection channel 451 is closed by using the valve 453. Next, the first cleaning channel 441 is opened by using the first cleaning valve 442, and the first cleaning solution is supplied to the separation chamber 220. When cleaning is completed, the second connection channel 461 is opened by using the valve 462, and a upper material on the first complex, such as the first cleaning solution, is discharged to the first waste chamber 240 through the second channel 461. Then, the first complex may be directly recovered from the separation chamber 220, or the first complex may be moved to the first recovering chamber 230, and then the first complex may be recovered to the first recovering chamber 230. In this regard, the first complex with a high purity may be obtained. Although not shown in FIG. 3, in order to perform the cleaning process twice, the first cleaning solution chamber 250 and the separation chamber 220 may be connected by at least two cleaning solution channels each including a normally closed valve, and the separation chamber 220 and the first waste chamber 240 may be connected by at least two connection channels each including a normally closed valve and a normally open valve. At least two cycles of the cleaning may be performed by sequentially opening the cleaning channels and the connection channels.

[The Second Enriching Unit]

Referring to FIG. 2, the second enriching unit 300 may receive a second fluid including the second target material from the sample chamber 100 and separate the second target material from the second fluid. In the second enriching unit 300, the second fine particles are attached to the second target material to form a second target material-second fine particle complex, i.e., a second complex, and thus the second complex may be separated from the second fluid. In this regard, the second enriching unit 300 includes a second particle chamber 310 housing the second fine particles.

At least one ligand that is specific to a surface marker of the second target material may be connected to a second fine particle. The second fine particle may bind to the second target material to increase the density of the second target material. The second fine particle may have a density that may cause a difference between the density of the second target material in the sample and the density of the remaining materials other than the second target material. For example, when miRNA is to be separated from plasma, the second fine particle with an appropriate density may be selected in consideration of densities of the plasma and other materials that may be included in the plasma. The second fine particle may be, for example, selected from the group consisting of a polystyrene particle, a polymethylmetaacrylate particle, a latex particle, an acrylonitril-butadiene-styrene copolymer (ABS) particle, a cyclic olefin copolymer particle, a melamine particle, and a composite thereof, as the first fine particle. The second fine particle may be a microparticle or a nanoparticle. The second fine particle may be a magnetic particle or a non-magnetic particle.

The second target material may be a material existing in a plasma layer. The second target material may be a microvesicle, micro RNA, DNA, lipid particle, or a combination thereof. The surface marker may be selected from the group consisting of a sugar, protein, lipid, or a combination thereof. The surface marker may be, for example, CD9, CD63, CD81, CD82, CD83, Fas Ligand, HER2, EGFR, EpCAM, or a combination thereof.

A second particle chamber 310 is connected to the sample chamber 100 by a second sample channel 511. The second sample valve 512 is prepared in the second sample channel 511 to control the flow of a fluid. The sample valve 512 may be a normally closed valve. The second target material and the second fine particle contact each other in the second particle chamber 310, and as the second fine particles are attached to the second target material, a second target material-second fine particle complex (a second complex) is formed. The second particle chamber 310 may have an inlet (not shown) for loading the second fine particles. When the microfluidic apparatus 1 is manufactured for a predetermined task, second fine particles suitable for the task may be housed in advance in the second particle chamber 310 in the manufacturing procedure of the microfluidic apparatus 1.

The second enriching unit 300 may further include a second recovering chamber 320 housing the second complex. The second recovering chamber 320 is connected to the second particle chamber 310 by a second recovering channel 521. A second recovering valve 522 is prepared in the second recovering channel 521 to control the flow of a fluid. The second recovering valve 522 may be a normally closed valve. Also, the second recovering valve 522 may be an open-close valve. The second recovering chamber 320 is disposed outside the second particle chamber 310 in the radial direction from the rotation center RC. The second complex gathers in the lowest layer of the second particle chamber 310, and when the second recovering channel 521 is opened by the second recovering valve 522, the second complex may be flowed into the second recovering chamber 320 due to a centrifugal force. For example, the second complex gathered in the lowest layer is extracted through an extraction hole by using a pipette, and thus the second complex may be separated from the second fluid. When the second recovering valve 522 is an open-close valve, the second recovering channel 521 may be dosed before the second complex is recovered from the second recovering chamber 320.

The second enriching unit 300 may further include a second waste chamber 330. The second waste chamber 330 may be connected to the second particle chamber 310 by the second discharge channel 531. A second discharge valve 532 is prepared in the second discharge channel 531 to control the flow of a fluid. The second discharge valve 532 may be a normally dosed valve. The second discharge channel 531 is provided to discharge a fluid in upper layers that are located on a top of the lowest layer including the second complex among the layers separated by the centrifugation in the second particle chamber 310. Therefore, the second discharge channel 531 is connected to the second particle chamber 310 located closer to the rotation center RC than the second recovering channel 521. Due to such structure, the upper layer material other than the second complex gathered in the lowest layer of the second particle chamber 310 may be discharged to the second waste chamber 330 through the second discharge channel 531, and then, the second complex may be recovered to the second recovering chamber 320 by opening the second recovering channel 521.

Referring to FIG. 3, the second enriching unit 300 may further include a second cleaning solution chamber 340. A second cleaning solution is housed in the second cleaning solution chamber 340. The second cleaning solution is provided to increase a degree of purity of the second complex before recovering the second complex to the second recovering chamber 320. The second cleaning solution chamber 340 is connected to the second particle chamber 310 by a second cleaning channel 541. A second cleaning valve 542 is prepared in the cleaning channel 541 to control the flow of a fluid. The second cleaning valve 542 may be a normally dosed valve. In this regard, the second discharge channel 531 may include a first connection channel 551 connecting the second particle chamber 310 and the second waste chamber 330, and a second connection channel 561 that is branched from the first connection channel 551 and connected to the second waste chamber 330. Valves 552 and 553 may be prepared at different locations in the first connection channel 551. The valve 452 located closer to the second particle chamber 310 may be a normally closed valve, the valve 553 relatively far from the second particle chamber 310 may be a normally open valve. A valve 562 is prepared in the second connection channel 561. The valve 562 is a normally closed valve.

Due to such a structure, when the second complex gathers in the lowest layer of the second particle chamber 310 based on a density gradient, the first connection channel 551 may be opened by using the valve 552, and thus the upper layer material on the second complex, such as a fluid of the upper, may be discharged to the second waste chamber 330 through the first connection channel 551. Then, the first connection channel 551 is closed by using the valve 553. Next, the second cleaning channel 541 is opened by using the second cleaning valve 542, and the second cleaning solution is supplied to the second particle chamber 310. When cleaning is completed, the second connection channel 561 is opened by using the valve 562, and the upper layer material of the second complex, such as the second cleaning solution, is discharged to the second waste chamber 330 through the second channel 561. Then, the second complex may be moved to the second recovering chamber 320, and then the second complex may be recovered to the second recovering chamber 320. In this regard, the second complex with a high purity may be obtained.

In order to perform the cleaning process twice, the second cleaning solution chamber 340 and the second particle chamber 310 may be connected by at least two cleaning solution channels each including a normally closed valve, and the second particle chamber 310 and the second waste chamber 330 may be connected by at least two connection channels each including a normally closed valve and a normally open valve. At least two cycles of the cleaning may be performed by sequentially opening the cleaning channels and the connection channels. For example, as shown in FIG. 3, three of the second cleaning solution channels 541 are located at different locations from the rotation center RC and connect the second cleaning solution chamber 340 and the second particle chamber 310. Also, the second particle chamber 310 and the second waste chamber 330 are connected by pairs of the first and second connection channels 551 and 561. The channels may be sequentially opened starting from the second cleaning channel 541, which is closest from the rotation center RC in a radial direction. Due to such a structure, three cycles of the cleaning process may be performed after discharging the upper layer fluid.

In the microfluidic apparatus 1 shown in FIGS. 2 and 3, the first and second sample channels 411 and 511 are opened by supplying energy to the first and second sample valves 412 and 512 after stopping rotation of the microfluidic apparatus in order to provide the first fluid layer including the first target material and the second fluid layer including the second target material to the first and second particle chambers 210 and 310 after centrifuging the sample in the sample chamber 100 to have a plurality of layers based on a density gradient. Since the microfluidic apparatus 1 is not rotated in this process, a centrifugal force is not applied to the sample housed in the sample chamber 100, and after some time elapses, the plurality of layers may be slowly mixed due to molecular motions in the sample. Such mixing of the plurality of layers may cause degradation of separation efficiency of the first and second target materials. Thus, to decrease a possibility of the mixing after centrifugation, a partition wall 600 is included in the sample chamber 100 as shown in FIGS. 2 and 3.

Figure 4:
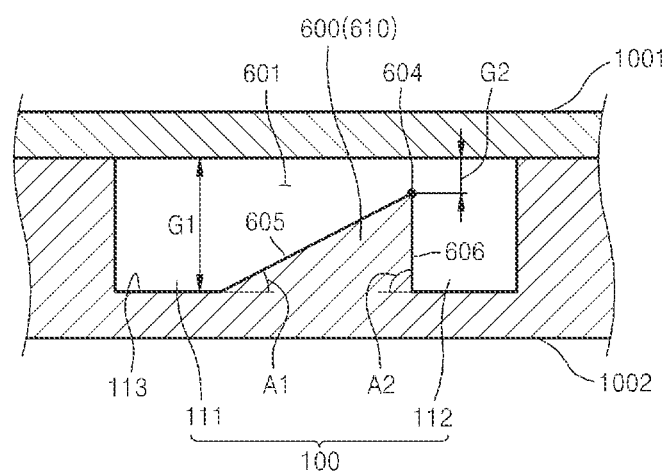
FIG. 4 is a cross-section taken along line A-A' of FIGS. 2 and 3.

FIG. 4 is a cross-sectional view of taken along line A-A' of FIG. 2 or 3. Referring to FIG. 4, the sample chamber 100 includes the partition wall 600 to partially restrict the flow of the sample in the radial direction. The partition wall 600 may extend from a bottom wall 1002 of the sample chamber 100 to a top wall 1001 of the sample chamber 100. The partition wall 600 may occupy a portion of the width of the sample chamber 100 in the circumference direction of the sample chamber 100. The partition wall 600 may occupy the entire width of the sample chamber 100 in the circumference direction of the sample chamber 100. Due to the partition wall 600, the sample chamber 100 is divided into an inner region 111, which is relatively close to the rotation center RC in the radial direction, and an outer region 112, which is relatively far from the rotation center RC in the radial direction. The partition wall 600 and the top wall 1001 may form a bottleneck portion 601 therebetween. The bottleneck portion 601 may connect the inner region 111 to the outer region 112. Although not shown in FIG. 4, the partition wall 600 may extend from the top wall 1001 of the sample chamber 100 to the bottom wall 1002 of the sample chamber 100 to form the bottleneck portion 601 between the partition wall 600 and the bottom wall 1002.

During centrifugation of a sample, due to the centrifugal force, the sample flows from the inner region 111 to the outer region 112 across the bottleneck portion 601 to form a plurality of layers based on density gradient in the sample chamber 100. When the microfluidic apparatus 1 is stopped from rotating, and thus, the centrifugal force disappears, the bottleneck portion 601 may restrict the movement of the sample between the inner region 111 and the outer region 112. That is, the flow of a fluid in the radial direction in the sample chamber 110 is restricted by the partition wall 600, and thus, a possibility of the mixing of the plurality of layers that are separated by centrifugation may decrease. Inner and outer gaps G1 and G2 of the bottleneck portion 601, that is, a gap between the bottleneck portion 601 and the top wall 1001 may have a size or dimension that is greater than a size or dimension of a gap that would induce a capillary phenomenon in order to enable the flow of a fluid through the bottleneck portion 601. If a capillary phenomenon occurs in the bottleneck portion 601, the bottleneck portion 601 is clogged, thereby making the flow of the fluid difficult during centrifugation. According to the present embodiment, the inner and outer gaps G1 and G2 of the bottleneck portion 401 may have a size or dimension that is greater than a size or dimension of a gap that would induce a capillary phenomenon, and during centrifugation, the fluid smoothly moves from the inner region 111 to the outer region 112 due to the centrifugal force, and after the centrifuging, the flow of the fluid between the inner region 111 and the outer region 112 may be partially restricted due to the relatively narrow inner and outer gaps G1 and G2.

During centrifugation, the sample needs to smoothly flow from the inner region 111 to the outer region 112. In one embodiment, the partition wall 600 may be formed in such a way that the bottleneck portion 601 is narrower from an inner portion of the sample chamber 100 to an outer portion of the sample chamber 100. That is, a fluid passage formed by the bottleneck portion 601 may have the inner gap G1 that is wider than the outer gap G2. During centrifugation, the sample flows from the inner region 111 to the outer region 112 due to the centrifugal force, that is, the sample may pass through the bottleneck portion 601 from the wider inner gap Cl to the narrower outer gap G2 to reach the outer region 112. However, when centrifugation is stopped, the centrifugal force disappears, and thus the sample does not smoothly pass through the bottleneck portion 601 due to the narrow outer gap G2. Thus, during centrifugation, the sample may relatively smoothly flow from the inner region 111 to the outer region 112, and when centrifugation is stopped, a flow of the sample from the outer region 112 to the inner region 111 is reduced or restricted. The shape of a cross-section of the partition wall 600 for forming the bottleneck portion 601 may be triangle with an apex 604 as illustrated in FIG. 4. In this regard, an inclined angle A2 of a hypotenuse 606 of the outer region 112 is greater than an inclined angle A1 of a hypotenuse 605 of the inner region 111. Such a structure may easily restrict the flow of the sample from the outer region 112 to the inner region 111. In addition, since the hypotenuse 605 and the bottom surface 113 of the inner region 111 do not have a step therebetween, the sample may more smoothly flow from the inner region 111 to the outer region 112 during centrifugation.

Figure 5:
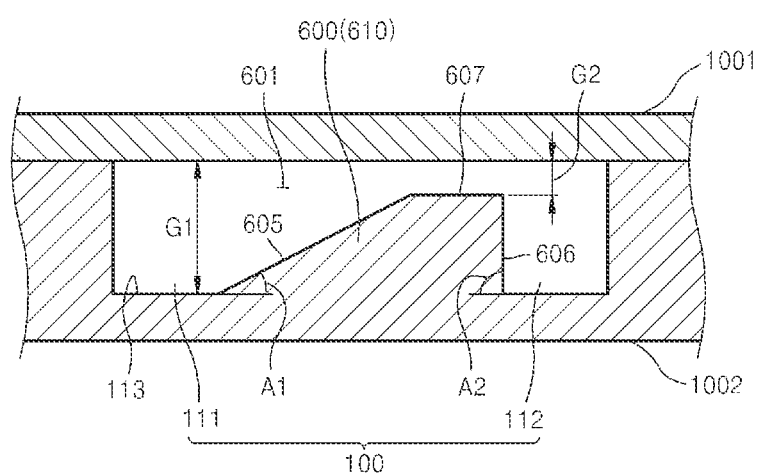
FIG. 5 is a cross-sectional view of an example of a bottleneck portion.

Although the partition wall 600 illustrated in FIG. 4 has a triangular cross-section, embodiments are not limited thereto. As illustrated in FIG. 5, the cross-section of the partition wall 600 may be a trapezoid having the hypotenuses 605 and 606 and a top surface 607 parallel to the top wall 1001. In addition, the cross-section of the partition wall 600 may have various other shapes as long as a size or dimension of the minimal gap of the bottleneck portion 601 is greater than a size or dimension of the gap that would induce a capillary phenomenon.

For example, when blood is centrifuged in the sample chamber 100, a plasma layer, a white blood cell layer, and a red blood cell layer are sequentially located in a direction from the inner portion to the outer portion of the sample chamber 100. The partition wall 600 may be located between the plasma layer and the white blood cell and circulating cancer cell layer. The first target material, for example, a circulating cancer cell, is located in the white blood cell layer, and the second target material, for example, miRNA, is located in the plasma layer. The partition wall 600 may be located between the plasma layer and the white blood cell layer. That is, the partition wall 600 may partition the sample chamber 110 in such a way that the plasma layer is located in the inner region 111 and the white blood cell layer and the red blood cell layer are located in the outer region 112. According to another embodiment, the partition wall 600 may partition the sample chamber 100 in such a way that the hypotenuse 606 of the outer region 112 of the partition wall 600 is located between the plasma layer, and the white blood cell and circulating cancer cell layer. By doing so, a possibility for mixing the plasma layer containing a protein inhibiting the binding between a circulating cancer cell and the first fine particle with a layer containing a circulating cancer cell after centrifugation may decrease.

Figure 6:
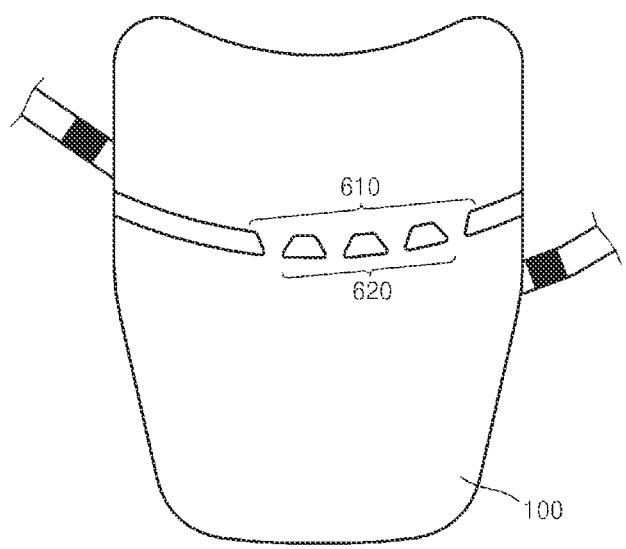
FIG. 6 is a plan view of a sample chamber including a partition wall and an opening.

FIG. 6 illustrates a partition wall for restricting a move of the sample in the radial direction according to another embodiment. Referring to FIG. 6, a plurality of partition walls 610 are spaced apart from each other in the circumference direction of the sample chamber 100 to form at least one opening 620 between the partition was 610, A width of the opening 620 may be, for example, in a range of about 200 μm to about 1 cm. The partition walls 610 may have identical lengths, and at least one of the partition walls 610 may have a length that is different from those of the other partition walls 610. For example, the partition walls 610 may extend from the bottom wall 1002 to the top wall 1001. Due to the partition walls 610, the sample chamber 100 is divided into an inner region 111, which is relatively close to the rotation center RC in the radial direction, and an outer region 112, which is relatively far from the rotation center RC in the radial direction. The opening 620 may connect the inner region 111 to the outer region 112.

As illustrated in FIG. 6, the opening 620 may be narrower from the inner portion to the outer portion of the sample chamber 100. Due to such a structure, the sample may relatively smoothly flow from the inner region 111 to the outer region 112, and a flow of the sample in the reverse direction thereof may be restricted. Furthermore, at least one of the partition walls 610 may form the bottleneck portion 601 together with the top wall 1001 as illustrated in FIGS. 4 and 5. Although not illustrated in FIG. 6, the partition walls 610 may extend from the top wall 1001 to the bottom wall 1002 of the sample chamber 100.

Figure 7A:
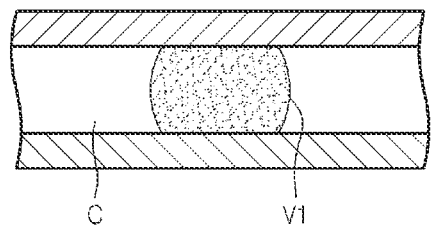
FIGS. 7A and 7B are cross-sectional views of a normally closed valve according to an embodiment.
Figure 7B:
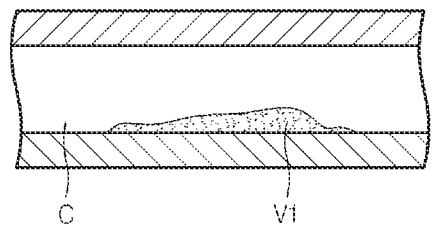

FIGS. 7A and 7B are cross-sectional views illustrating examples of a normally closed valve. The normally closed valve may include a valve material V1 that is in a solid state at room temperature and thus clogs a channel C as illustrated in FIG. 7A. The valve material V1 melts at high temperature and moves within the channel C, and as illustrated in FIG. 7B, the valve material V1 returns to the solid state while the channel C is being opened. Energy irradiated from the outside may be, for example, an electromagnetic wave, and an energy source may be a laser beam source that irradiates a laser beam, a light emitting diode that irradiates visible light or infrared light, or an Xenon lamp. When a laser beam source is used, the laser beam source may include at least one laser diode. An external energy source may be selected according to a wavelength of an electromagnetic wave that is absorbable by exthothermic particles included in the valve material V1. As a valve material V1, a thermoplastic resin, such as a cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF) may be used. In addition, as the valve material V1, a phase change material that exists in a solid state at room temperature may be used. The phase change material may be wax. When heated, wax dissolves into a liquid state and a volume thereof expands. Examples of the wax are paraffin wax, microcrystalline wax, synthetic wax, and natural wax. The phase change material may be a gel or a thermoplastic resin. As the gel, polyacrylamide, polyacrylates, polymethacrylates, or polyvinylamides may be used. A plurality of fine exthothermic particles that absorb electromagnetic wave energy and emits heat, may be dispersed in the valve material V1. Fine exthothermic particles may have an average particle size of about 1 nm to about 100 μm to freely pass the fine channel C having a depth of about 0.1 mm and a width of about 1 mm. Fine exthothermic particles may have an exthothermic property, and thus, when electromagnetic wave energy is supplied by, for example, exposure to laser light, a temperature thereof increases rapidly, and the fine exthothermic particles may homogeneously disperse in wax. To obtain such a property, each of the fine exthothermic particles may have of a core including a metallic component and a hydrophobic surface structure. For example, the fine exthothermic particles may each have a molecular structure in which a plurality of surfactants are connect to and cover a Fe-core. The fine exthothermic particles may be preserved in a dispersion state in carrier oil. The carrier oil may also be hydrophobic to allow the fine exthothermic particles having a hydrophobic surface structure to be homogeneously dispersed. Carrier oil with the fine exthothermic particles dispersed therein is mixed with a molten phase change material, and the mixture is loaded into the channel C and solidified to dog the channel C. The fine exthothermic particles are not limited to the polymer particles presented as an example of the fine exthothermic particles, and quantum dots or magnetic beads may also be used as fine exthothermic particles. In addition, the fine exthothermic particles may be, for example, a fine metal oxide, such as $Al_2O_3$, $TiO_2$, $Ta_2O_3$, $Fe_2O_3$, $Fe_3O_4$, or, $HfO_2$. In addition, no fine exthothermic particles may be necessarily included in the dosed valve, and according to another embodiment, the dosed valve may be a phase change material without any fine exthothermic particles.

Figure 8A:
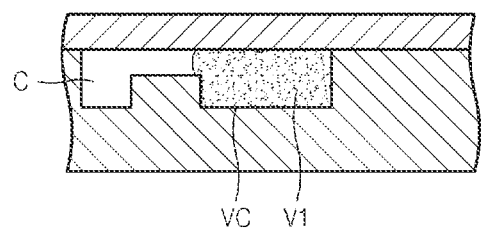
FIGS. 8A and 8B are cross-sectional views of a normally open valve according to an embodiment.
Figure 8B:
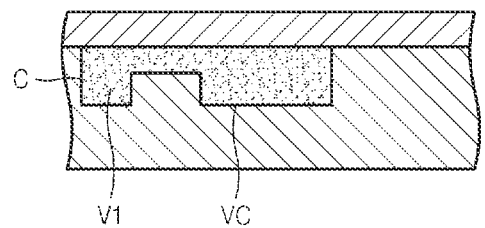

FIGS. 8A and 8B are cross-sectional views of an example of a normally open valve. The open valve includes a channel C, a valve chamber VC extending from the channel C in a width direction of the channel C, and a valve material V1 filling the valve chamber VC. As illustrated in FIG. 8A, before external energy is supplied to the valve material V1, the channel C is maintained open because the valve material V1 exists in the valve chamber VC. However, when external energy is supplied to the valve material V1, the valve material V1 melts and expands, thereby flowing into the channel C and solidifying therein, thereby blocking the flow of the fluid through the channel C.

Figure 9A:
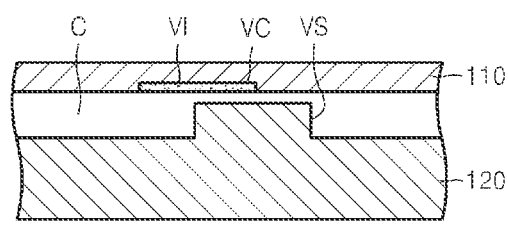
FIGS. 9A, 9B, and 9C are cross-sectional views of an open/close valve according to an embodiment.
Figure 9B:
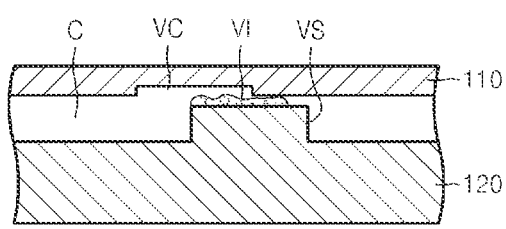
Figure 9C:
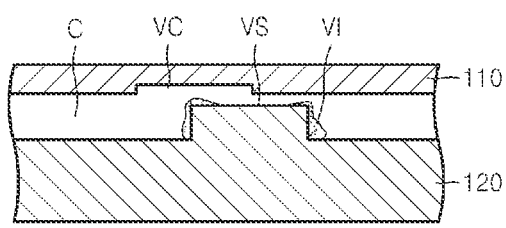

FIGS. 9A to 9C are cross-sectional views of an example of an open/close valve. Referring to FIG. 9A, the open/close valve includes a channel C, a valve chamber VC located at a higher level than the channel C, a valve material V1 filling the valve chamber VC, and a step VS that partially overlaps with and protrudes toward the valve chamber VC under the valve chamber VC in the channel C. As illustrated in FIG. 9A, before external energy is supplied to the valve material V1, the channel C is maintained open because the valve material V1 exists in the valve chamber VC. When external energy is supplied to the valve material V1, the valve material V1 melts and expands, thereby flowing onto the step VS, and then, the valve material V1 is solidified, thereby blocking the flow of the fluid through the channel C as illustrated in FIG. 9B. When a stronger external energy is supplied to the solidified valve material V1, the valve material V1 located on the step VS melts and becomes fluid. Thus, the valve material V1 flows into the channel C over the step VS. As a result, as illustrated in FIG. 9C, the channel C is re-opened.

EXAMPLE

Hereinafter, a method of enriching a target material by using the microfluidic apparatus 1 according to an embodiment will be described. In the present embodiment, blood is used as a sample, and circulating cancer cells and miRNA included in the blood are separated.

[Preparation]: Blood including circulating cancer cells and miRNA, as the first and second materials, is loaded into the sample chamber 100. The first and second fine particles that are specifically connected to the first and second materials are respectively loaded into the first and second particle chambers 210 and 310. In the current embodiment, the first fine particles are connected to circulating cancer cells to induce a density difference from white blood cells, thereby allowing the separation of only cancer cells from blood. The first fine particles may be, for example, melamine particles, and a density thereof may be, for example, about 1.57 g/cm$^3$, which is greater than the density of biological particles in blood, that is, about 1.05 g/cm$^3$ to about 1.1 g/cm$^3$. The second fine particles induce a difference in a sinking rate between the plasma and miRNA and may have a density that induces a density difference. A miRNA-bondable material is fixed on surfaces of the second fine particles, wherein the miRNA-bondable material is, for example, a material that electrically binds to miRNA or polynucleotide that is complementary to miRNA. In addition, appropriately selected DGM is loaded into the separation chamber 210. If needed, the first and second cleaning solutions may each respectively loaded into the first and second cleaning solution chamber 250 and 340. The first and second cleaning solutions may be Tween20, Triton X-100, DMSO, a buffer including a combination thereof, PBS, or a combination thereof.

[Centrifugation of blood]: The microfluidic apparatus 1 is mounted on the rotation driving unit 10, and then, rotated at a rotation rate of, for example, about 4000 rpm for about 5 minutes. By doing so, the blood in the sample chamber 100 may be divided into a plurality of layers based on a density difference. A red blood cell layer containing the heaviest red blood cell is located farthest away in the radial direction from the rotation center RC. Then, a target layer and a plasma layer are sequentially located closer to the rotation center RC. Since physical properties of white blood cell and a density of cancer cells are similar, the white blood cell and cancer cells may be located in the same layer when the centrifugation based on a density gradient is performed. Since proteins in blood are lighter than blood corpuscles, the proteins are located in the plasma layer. Thus, miRNA is located in the plasma layer.

[Discharge of plasma]: The microfluidic apparatus 1 is stopped from rotating, and by using the electromagnetic wave generator 20, an electromagnetic wave, for example, a laser beam, is irradiated to the second sample valve 512 to open the second sample channel 511. Then, when the microfluidic apparatus 1 is rotated again, the plasma is moved to the second particle chamber 310 through the second sample channel 511 due to a centrifugal force. Here, miRNA may be moved together with the plasma to the second particle chamber 310.

[Discharge of white blood cell layer]: The microfluidic apparatus 1 is stopped from rotating, and by using the electromagnetic wave generator 20, an electromagnetic wave, for example, a laser beam, is irradiated to the first sample valve 412 to open the first sample channel 411. Then, when the microfluidic apparatus 1 is rotated again, the white blood cell layer is moved to the first particle chamber 210 due to a centrifugal force. Here, the circulating cancer cells may be moved together with the white blood cells to the first particle chamber 210.

While the valves are opened in a state where the microfluidic apparatus 1 is stopped from rotating, a possibility for mixing the white blood cell layer and the plasma layer may be decreased by using the partition wall 600 or 610.

[Formation of first complex]: The microfluidic apparatus 1 is rotated in clockwise and counterclockwise directions for a predetermined period of time, for example, about 1 hour, as a shaking process, to bring the first fine particles in contact with the circulating cancer cells. Then, the first fine particles are attached to the circulating cancer cells, and thus the first complex is formed in the first particle chamber 210.

[Separation of the first complex using a density difference]: By using the electromagnetic wave generator 20, a laser beam is irradiated to the separation valve 422 to open the separation channel 421. When the microfluidic apparatus 1 is rotated, the fluid including the first complex is moved to the separation chamber 220 due to a centrifugal force. Then, when the microfluidic apparatus 1 is rotated for about 10 minutes for example, at about 4000 rpm, the first complex is moved to the lowest layer of the separation chamber 220 due to a density difference between the first complex and the DGM.

[Recovering of the first complex]: The microfluidic apparatus 1 is stopped from rotating, and then, the first complex is extracted from the separation chamber 220 through an extraction hole (not shown) by using, for example, a pipette. In this regard, the circulating cancer cells in blood may be separated and enriched.

The first complex may be moved to the first recovering chamber 230. An electromagnetic wave, for example, a laser beam is irradiated to the first recovering valve 432 by using the electromagnetic wave generator 20 to open the first recovering channel 431. The microfluidic apparatus 1 is rotated for about 30 seconds for example, at about 4000 rpm to move the first complex to the first recovering chamber 230 from the fluid housed in the separation chamber 220. The microfluidic apparatus 1 is stopped from rotating, and then, the first complex is extracted from the first recovering chamber 230 through an extraction hole (not shown) by using, for example, a pipette.

The first complex may be recovered after discharging materials other than the first complex in the separation chamber 220 to the first waste chamber 240. For example, by using the electromagnetic wave generator 20, an electromagnetic wave, for example, a laser beam, is irradiated to the first discharge valve 434 to open the first discharge channel 433. The microfluidic apparatus 1 is rotated to discharge the DGM and other fluids located in an upper part of the first complex from the fluids housed in the separation chamber 220 to the first waste chamber 240. Then, the microfluidic apparatus 1 is stopped from rotating, and then, the first complex is extracted from the separation chamber 220 through an extraction hole (not shown) by using, for example, a pipette. Furthermore, the first complex may be first moved to the first recovering chamber 230 and then extracted from the first recovering chamber 230.

When the microfluidic apparatus 1 illustrated in FIG. 3 is used, a cleaning process may be performed before recovering the first complex. After separation of the first complex using a density difference is performed, the first connection channel 451 may be opened by operating the valve 452, the upper layer material in the separation chamber 220 may be discharged to the first waste chamber 240, and the first connection channel 451 may be closed by operating the valve 453. Then, the first cleaning channel 441 may be opened by operating the first cleaning valve 442. The first cleaning solution is transferred to the separation chamber 220 from the first cleaning solution chamber 250 by rotating the microfluidic apparatus 1. If needed, after performing the shaking process, the second connection channel 461 may be opened by operating the valve 462, and the first cleaning solution may be discharged to the first waste chamber 240. Then, the first complex is recovered from the separation chamber 220 or from the first recovering chamber 230.

[Formation of second complex]: During the formation of the first complex, the second fine particles and the plasma are already shaken in the second particle chamber 310. Additionally, the shaking process may be, for example, performed for about 1 to about 3 hours. In this regard, as the second fine particles are attached to miRNA, the second complex is formed in the second particle chamber 310, and the second complex gathers in the lowest layer of the second particle chamber 310.

[Discharge of fluid]: By using the electromagnetic wave generator 20, an electromagnetic wave, for example, a laser beam, is irradiated to the second discharge valve 532 to open the second discharge channel 531. Then, the microfluidic apparatus 1 is rotated to discharge the fluid located in an upper part of the second complex from the fluids housed in the second particle chamber 310 to the second waste chamber 330.

[Recovering of the second complex]: Next, the second recovering channel 521 is opened by operating the second recovering valve 522, the second complex is moved to the second recovering chamber 320, and then the second complex may be extracted from the second recovering chamber 320. In this regard, miRNA may be separated from blood and enriched.

When the microfluidic apparatus 1 illustrated in FIG. 3 is used, a cleaning process may be performed before recovering the second complex. After formation of second complex is performed, the first connection channel 551 may be opened by operating the valve 552, the upper layer material of the second complex in the second particle chamber 310 may be discharged to the second waste chamber 330, and the first connection channel 551 may be dosed by operating the valve 553. Then, the second cleaning channel 541 is opened by operating the second cleaning valve 542. The second cleaning solution is transferred to the separation chamber 220 from the second cleaning solution chamber 340 by rotating the microfluidic apparatus 1. If needed, after performing the shaking process, the second connection channel 561 may be opened, the second complex is moved to the second recovering chamber 320, and then the second complex may be recovered from the second recovering chamber 320.

By doing so, circulating cancer cells and miRNA in a plasma layer of blood may be separated and enriched by using one microfluidic apparatus.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A microfluidic apparatus mounted on a rotation driving unit, the microfluidic apparatus comprising:
   a sample chamber that receives a biological sample and separates the biological sample into a first fluid layer comprising a first target material and a second fluid layer comprising a second target material using centrifugal force;
   a first sample channel connected to the sample chamber at a first location on the sample chamber;
   a second sample channel connected to the sample chamber at a second location on the sample chamber, wherein the first location is located further away from a rotation center of the apparatus than the second location;
   a first enriching unit connected to the sample chamber by the first sample channel and comprising a first fine particle that specifically binds to the first target material, wherein the first enriching unit receives the first fluid layer from the sample chamber via the first sample channel, wherein the first fine particle and the first target material form a first complex comprising the first fine particle and the first target material, and wherein the first enriching unit separates the first complex from the first fluid layer using a density difference with a density-gradient material (DGM) having a lower density than the first complex; and
   a second enriching unit connected to the sample chamber by the second sample channel, wherein the second enriching unit receives the second fluid layer from the sample chamber via the second sample channel, forms a second complex of a second fine particle and the second target material, and separates the second complex from the second fluid layer using a density difference between the second fluid layer and the second complex.

2. The microfluidic apparatus of claim 1, wherein the first enriching unit comprises:
   a first particle chamber that houses the first fine particle and is connected to the sample chamber by the first sample channel to receive the first fluid layer from the sample chamber;
   a separation chamber that houses the DGM and is connected to the first particle chamber by a separation channel to receive the first fluid layer including the first complex; and
   a first recovering chamber that is connected to the separation chamber by a first recovering channel to receive the first complex separated from the first fluid layer.

3. The microfluidic apparatus of claim 2, wherein the first enriching unit further comprises a first waste chamber that is connected to the separation chamber by a first discharge channel to receive a fluid above the first complex in the separation chamber.

4. The microfluidic apparatus of claim 2, wherein the first enriching unit further comprises:
   a first cleaning solution chamber that houses a first cleaning solution and is connected to the separation chamber by a first cleaning channel to supply the first cleaning solution to the separation chamber; and
   a first waste chamber that is connected to the separation chamber by a plurality of connection channels to receive a fluid above the first complex in the separation chamber.

5. The microfluidic apparatus of claim 2, wherein the second enriching unit comprises:

a second particle chamber that houses the second fine particle and is connected to the sample chamber by the second sample channel to receive the second fluid layer from the sample chamber; and a second recovering chamber that is connected to the second particle chamber by a second recovering channel to receive the second complex separated from the second fluid layer.

6. The microfluidic apparatus of claim 5, wherein the second enriching unit further comprises a second waste chamber that is connected to the second chamber by a second discharge channel to receive a fluid above the second complex in the second particle chamber.

7. The microfluidic apparatus of claim 5, wherein the second enriching unit further comprises:

a second cleaning solution chamber that houses a second cleaning solution and is connected to the second particle chamber by a second cleaning channel to supply the second cleaning solution to the second particle chamber; and the second waste chamber that is connected to the second particle chamber by a plurality of connection channels to receive a fluid above the second complex in the second particle chamber.

8. The microfluidic apparatus of claim 1, wherein the sample is blood, the first fluid layer is a white blood cell layer, and the second fluid layer is a plasma layer.

9. The microfluidic apparatus of claim 1, wherein the first target material is a circulating tumor cell, a cancer stem cell, or a cancer cell.

10. The microfluidic apparatus of claim 1, wherein the second target material is nano (or micro)-vesicles, miRNA, DNA, or sub-micron sized lipid particles.

11. The microfluidic apparatus of claim 1, wherein a partition wall is provided in the sample chamber to form a bottleneck portion together with at least one of a top wall and a bottom wall of the sample chamber to partially restrict the flow of the biological sample in a radial direction of the sample chamber, and a gap between the bottleneck portion and the at least one of the top wall and the bottom wall is greater than a gap that would induce a capillary phenomenon.

12. The microfluidic apparatus of claim 11, wherein the partition wall has such a shape that the bottleneck portion is narrower at an inner portion of the sample chamber than at an outer portion of the sample chamber in the radial direction of the sample chamber.

13. The microfluidic apparatus of claim 11, wherein a plurality of partition walls are arranged in a circumference direction of the sample chamber and the partition walls are spaced apart from each other with openings therebetween.

14. The microfluidic apparatus of claim 13, wherein each of the openings is narrower at an inner portion of the sample chamber than at an outer portion of the sample chamber in the radial direction.

* * * * *